United States Patent [19]

Kopp et al.

[11] Patent Number: 4,757,105

[45] Date of Patent: Jul. 12, 1988

[54] PROCESS FOR THE PRODUCTION OF FINELY DIVIDED POLYISOCYANATES CONTAINING UREA GROUPS

[75] Inventors: Richard Kopp, Cologne; Gerhard Grögler; Heinrich Hess, both of Leverkusen; Klaus König, Odenthal, all of Fed. Rep. of Germany

[73] Assignee: Bayer Aktiengesellschaft, Leverkusen, Fed. Rep. of Germany

[21] Appl. No.: 116,108

[22] Filed: Nov. 3, 1987

[30] Foreign Application Priority Data

Nov. 8, 1986 [DE] Fed. Rep. of Germany ....... 3638148

[51] Int. Cl.$^4$ .............................................. C08L 75/00
[52] U.S. Cl. .................................... 524/714; 524/722; 524/723; 524/724; 528/52; 528/53; 252/182
[58] Field of Search ............... 524/714, 722, 723, 724; 528/52, 53; 252/182

[56] References Cited

U.S. PATENT DOCUMENTS 3,906,019 9/1975 Campbell et al. ................... 260/453
4,680,367 7/1987 Kopp et al. .......................... 528/44

Primary Examiner—Maurice J. Welsh
Attorney, Agent, or Firm—Gene Harsh; Joseph C. Gil; Thomas W. Roy

[57] ABSTRACT

The present invention is directed to a process for the preparation of finely divided solid polyisocyanates containing urea groups by reacting organic polyisocyanates which are free from urea groups with water in an aqueous emulsion, characterized in that the reaction is carried out in the presence of an emulsion- and dispersion-stabilizing compound.

22 Claims, No Drawings

PROCESS FOR THE PRODUCTION OF FINELY DIVIDED POLYISOCYANATES CONTAINING UREA GROUPS

BACKGROUND OF THE INVENTION

1. Field of the Invention

This invention relates to a process for the preparation of finely divided solid polyisocyanates containing urea groups by the reaction of organopolyisocyanates which are free from urea groups with water in the presence of a stabilizing compound containing at least one hydrophilic and at least one isocyanate reactive group and optionally in the presence of conventional emulsifiers and/or catalysts and/or bases.

2. Description of the Prior Art

Processes for the preparation of solid polyisocyanates containing urea groups by the reaction of organic polyisocyanates which are free from urea groups with an excess of water as reactive medium are already known (inter alia U.S. Pat. No. 3,906,019). Since in these processes the reaction products immediately cake together and are therefore difficult to work up and process, attempts have been made to prepare these reaction products in a finely divided form and in quantitative yields. According to the teaching of DOS No. 3,438,527, this object may be achieved by carrying out the reaction in the presence of a high molecular weight protective colloid such as a polyacrylate, cellulose, polyvinyl alcohol, etc. Although these high molecular weight protective colloids are highly effective, their solubility in water may cause long production runs. Moreover, the protective colloids are liable to be deposited as a film on the surface of the polyisocyanates containing urea groups, thereby impairing the reactivity of these polyisocyanates, especially if they are kept in storage for some time.

It is therefore an object of the present invention to provide a process for the preparation of polyisocyanates containing urea groups wherein the reaction products are not only obtained quantitatively in a very finely divided form but are also not impaired in their reactivity.

SUMMARY OF THE INVENTION

The present invention is directed to a process for the preparation of finely divided solid polyisocyanates containing urea groups by reacting organic polyisocyanates which are free from urea groups with water in an aqueous emulsion, characterized in that the reaction is carried out in the presence of an emulsion- and dispersion-stabilizing compound corresponding to the general formula (I)

$$(X)_a-R-(Y)_b \qquad (I)$$

wherein

X denotes a $NH_2$ group, a $NHR^1$ group in which $R^1$ stands for a $C_1$-$C_{10}$-alkyl residue, which contains optionally a tert. amino group, an OH-group or an SH-group.

R denotes an aromatic group containing 6 to 20, preferably 6 to 10 carbon atoms, a heteroaromatic group containing 5 to 20, preferably 6 to 10 carbon atoms and at least one oxygen and/or nitrogen atom in the ring system, an aliphatic group containing 2 to 20, preferably 2 to 10 carbon atoms or a cycloaliphatic group containing 4 to 20, preferably 4 to 10 carbon atoms, the above-mentioned groups being optionally substituted with halogen atoms such as chlorine or bromine, Y denotes COOH, $COO^-M^+$ in which M stands for an alkali metal, an alkaline earth metal, $NH_4$ or a $NH-(R^2)_3$ group in which $R^2$=hydroxyalkyl, alkoxyalkyl or alkyl with 1 to 10, preferably 1 to 4 carbon atoms $SO_3H$, $SO_3^-M^+$ in which M has the meaning previously indicated, $-N(R^2)_2$ or a $N^{\oplus}H(R^2)_2 Z^{\ominus}$ group in which $Z^{\ominus}$ denotes a carboxylate or sulphonate group and $R^2$ either has the meaning previously indicated, or stands for a group of general formula (II)

$$-(CH_2-CH_2-O)_{\overline{x}}(CH_2-CHO)_y-R_4 \qquad (II)$$
$$\phantom{-(CH_2-CH_2-O)_{\overline{x}}(CH_2-}|$$
$$\phantom{-(CH_2-CH_2-O)_{\overline{x}}(CH_2-}R^3$$

wherein $R^3$ denotes a $C_1$-$C_6$, preferably a $C_1$-$C_4$-alkyl group, $R^4$ denotes hydrogen or a $C_1$-$C_6$ alkyl group, preferably hydrogen or a $C_1$-$C_4$-alkyl group and x and y may be identical or different and each represent an integer with a value of 0 to 50, preferably 0 to 5 and wherein the sum of x+y is at least 1, a and b, which may be identical or different, each represent an integer with a value from 1 to 3, preferably 1 or 2, provided that when Y stands for OH or SH, R must not be an aromatic or heteroaromatic group and when Y stands for a group of the general formula (II), X may only stand for $NH_2$ or $NHR^2$ and R is a chemical bond, or the reaction may be carried out in the presence of an alkali metal hydrogen sulphite, preferably sodium hydrogen sulphite.

DETAILED DESCRIPTION OF THE INVENTION

The starting polyisocyanates, which are free from urea groups and used for the process according to the invention, include aliphatic, cycloaliphatic, araliphatic, aromatic or heterocyclic polyisocyanates of the kind described, for example, by W. Siefken in Justus Liebigs Annalen der Chemie, 562, pages 75 to 136, for example those corresponding to the formula $$Q(NCO)_n,$$

wherein n=2 to 4, preferably 2 and

Q denotes an aliphatic hydrocarbon group having 2 to 18, preferably 6 to 10 carbon atoms, a cycloaliphatic hydrocarbon group having 4 to 15, preferably 5 to 10 carbon atoms, an aromatic hydrocarbon group having 6 to 15, preferably 6 to 13 carbon atoms, or an araliphatic hydrocarbon group having 8 to 15, preferably 8 to 13 carbon atoms.

Examples of these polyisocyanates include ethylene diisocyanate, 1,4-tetramethylene diisocyanate, 1,6-hexamethylene diisocyanate, 1,12-dodecane diisocyanate, cyclobutane-1,3-diisocyanate, cyclohexane-1,3- and -1,4-diisocyanate and any mixtures of their stereoisomers, 1-isocyanato-3,3,5-trimethyl-5-isocyanatomethyl cyclohexane (DE-Auslegeschrift No. 1,202,785, U.S. Pat. No. 3,401,190), 2,4- and 2,6-hexahydrotoluylene diisocyanate and any mixtures of these isomers, hexahydro-1,3- and/or -1,4-phenylene diisocyanate, perhydro-2,4'- and/or 4,4'-diphenylmethane diisocyanate, 1,3- and 1,4-phenylene diisocyanate, 2,4- and 2,6-toluylene diisocyanate and any mixtures of these isomers, diphenylmethane-2,4'-, -4,4'- and/or -2,2'-diisocyanate and naphthylene-1,5-diisocyanate.

Additional examples include triphenylmethane-4,4',4''-triisocyanate; polyphenyl-polymethylene polyisocyanates obtained by aniline-formaldehyde condensation followed by phosgenation such as those described in GB Patent Specification Nos. 874,430 and 848,671; perchlorinated aryl polyisocyanates as described, for example in DE-Auslegeschrift No. 1,157,601 (U.S. Pat. No. 3,277,138); norbornane diisocyanates according to U.S. Pat. No. 3,492,330; polyisocyanates containing allophanate groups as described, for example, in GB Patent Specification No. 994,890, BE Patent Specification No. 761,626 and NL Patent Specification No. 7,102,524; polyisocyanates containing isocyanurate groups as described, for example, in U.S. Pat. No. 3,001,973, DE Patent Specification Nos. 1,022,789, 1,222,067, and 1,027,394 and in DE-Offenlegungsschriften Nos. 1,929,034 and 2,004,048; polyisocyanates containing urethane groups, for example, as described in BE-Patent Specification No. 752,261 or in U.S. Pat. Nos. 3,394,164 and 3,644,457; polyisocyanates prepared by telomerization reactions as described, for example, in U.S. Pat. No. 3,654,106; polyiso-cyanates containing ester groups such as those mentioned, for example, in GB Patent Specification Nos. 965,474 and 1,072,956, U.S. Pat. No. 3,567,763 and DE Patent Specification No. 1,231,688; reaction products of the above-mentioned isocyanates with acetals according to DE Patent Specification No. 1,072,385; and polyisocyanates containing polymeric fatty acid esters according to U.S. Pat. No. 3,455,883. The commercially readily available polyisocyanates are in most cases particularly preferred, e.g. 2,4- and 2,6-toluylene diisocyanate and any mixtures of these isomers ("TDI"), polyphenyl-polymethylene polyisocyanates which are obtainable by aniline-formaldehyde condensation followed by phosgenation ("crude MDI") and polyisocyanates containing urethane groups, allophanate groups or isocyanurate groups ("modified polyisocyanates"), especially those modified polyisocyanates which are derived from 2,4- and/or 2,6-toluylene diisocyanate or from 4,4'-, 2,4'- and/or 2,2'-diphenylmethane diisocyanate. Toluylene-2,4-diisocyanate is especially preferred.

The polyisocyanates may be used in the form of a (concentrated) solution in a solvent which is inert towards the polyisocyanates and immiscible with water. These preferred solvents include aliphatic or aromatic hydrocarbons such as n-hexane, cyclohexane, isooctane, benzene, toluene, xylene or hydrophobic plasticizers.

The stabilizing, preferably low molecular weight compound, corresponding to the above general formula (I) is preferably a compound in which X and Y have the following meaning:

1.
   $X=NH_2$
   $Y=COOH$,
   e.g., 2-, 3-, or 4-aminobenzoic acid, 4-chloranthranilic acid, 6-chloranthranilic acid, 3-amino-4-methylbenzoic acid, 3-aminocinnamic acid, 5-aminoisophthalic acid, 3-aminosalicylic acid, 4-aminosalicylic acid, 5-aminosalicylic acid, aminoacetic acid, N-methylaminoacetic acid, 3-aminopropanoic acid, 4-aminobutanoic acid, 6-aminohexanoic acid, L(+)-2,6-diaminohexanoic acid, 11-aminoundecanoic acid, L(+)-aminobutane diacid, L(+)-aminopentane diacid and DL-methiamine.

2.
   $X=NH_2$
   $Y=COO^\ominus M^\oplus$,
   e.g. alkali metal and alkaline earth metal salts of the carboxylic acids mentioned under 1. above, salts of the above-mentioned carboxylic acids with tertiary amines, e.g. with trimethylamine, triethylamine, dimethylbenzylamine, tris-hydroxyethylamine, tris-[(2-hydroxyethoxy)ethyl]-amine and triethylene diamine.

3.
   $X=NH_2$
   $Y=SO_3H$
   e.g. 2-, 3-, and 4-aminobenzene sulphonic acid, 3-amino-6-chlorobenzene sulphonic acids, p-phenylenediamine-2-sulphonic acid, 4-aminotoluene-2-sulphonic acid, 5-aminotoluene-2-sulphonic acid, 2-aminotoluene-4-sulphonic acid, 3-aminobenzyl sulphonic acid, 4-aminobenzylsulphonic acid, naphthionic acid, 2-aminoethane sulphonic acid, 2-methylaminoethane sulphonic acid and 2-butylaminoethane sulphonic acid, 4.
   $X=NH_2$
   $Y=SO_3^\ominus M^\oplus$,
   e.g. alkali metal and alkaline earth metal salts of the sulphonic acids mentioned under 3. above, and salts of these sulphonic acids mentioned under 3. with the amines mentioned under 2., 5.
   $X=-NH_2, -NHR^1$
   $Y=-N(R^2)_2$
   1-Amino-3-(dimethylamino)propane, N-Bis(3-dimethylaminopropyl)amine, N-Methyl-N-(3-aminopropyl)-ethanolamine, N,N-Diethyl-1,3-propandiamine, Bis(3-aminopropyl-methylamine, 1-Amino-2-diethylaminoethane, 4-Amino-1-diethylaminopentane, 4-Amino-1-dimethylaminopentane, 1-Amino-2-dimethylaminoethane, 6.
   $X=NH_2$ or $OH$
   $Y=N^\oplus H(R^2)_2 Z^\ominus$
   e.g., ammonium salts of amines containing at least one OH group, one primary and/or secondary amino group and at least one tertiary amino group and a quantity of carboxylic or sulphonic acid such that at least one NCO-reactive group per molecule is not converted into salt form, preferably salts of N,N-dimethyl-1,3-propylene diamine and one equivalent of acetic acid, propionic acid, lactic acid, dimethylolpropionic acid, methane sulphonic acid, butane sulphonic acid or 2-hydroxy-ethanesulphonic acid; or salts of 2-(N,N-dimethylamino)ethanol, 2-(N,N-dimethylamino)isopropanol or 2-(N,N-dimethylaminoethoxy)-ethanol and carboxylic acids such as acetic acid, propionic acid, benzoic acid or lactic acid, 7.
   $X=OH$ or $SH$
   $Y=COO^\ominus M^\oplus$,
   e.g. salts of hydroxycarboxylic acids or mercaptocarboxylic acids such as lactic acid, glycollic acid, citric acid, dimethylolpropionic acid, tartaric acid, or mercaptoacetic acid and the amines mentioned under 2.; or 8. Sodium hydrogen sulphite.

To carry out the process according to the invention, a solution of water, the stabilizer according to the invention and the emulsifier and catalyst, if used, should first be prepared, for example by stirring the components together. These components form the aqueous phase of the reaction mixture. The polyisocyanate is then introduced into the aqueous phase either all at once or continuously. Alternatively, all the components may be added together at the same time, provided the emulsion or dispersion remains stable.

The stabilizing compound is preferably used in a quantity of about 0.01 to 5.0% by weight, most preferably about 0.01 to 2% by weight, based on the quantity of polyisocyanate. The quantity of organic polyisocyanate may vary about 1 to 75% by weight, preferably about 10 to 30% by weight and most preferably 15 to 25% by weight, based on the whole reaction mixture.

The usual apparatus are used for preparing the emulsion, e.g. ultrasound disintegrators or apparatus in which the streams of substances are projected at high speed from nozzles to be thrown against one another, parallel to one another or against solid surfaces. It is particularly preferred to use an apparatus in which the liquids are projected with high acceleration and shearing forces through grids or slots. Such apparatus are available commercially and known, for example, as mixing sirens. Apparatus operating on the rotor-stator principle are preferably used.

The emulsion is preferably prepared at about 10° to 50° C., most preferably at about 23° to 25° C. The polyisocyanates should be present in the aqueous phase with an average droplet size of about 0.5 to 200 μm, preferably about 0.5 to 20 μm.

After the emulsion has been prepared, the temperature for the reaction of the organic polyisocyanate with water should be maintained at about 10° to 80° C., preferably about 20° to 40° C. The reaction is preferably carried out at normal pressure although it may be carried out at reduced or elevated pressure in suitable apparatus. An elevated pressure may develop of its own accord due to the liberation of $CO_2$. The emulsion and the dispersion formed in the process should only be mildly agitated.

The polyisocyanates with urea groups formed in the reaction are only sparingly soluble in water and therefore cease to undergo further reaction so that the remaining isocyanate groups in the polyisocyanates do not react with the water in the reaction mixture and generally only one isocyanate group per molecule of the organic polyisocyanates put into the process is used up in the formation of a urea group. The isocyanate contents of the products obtained from the process according to the invention are in most cases only slightly below the calculated isocyanate content.

For the preparation of the emulsion, the aqueous or continuous phase may contain conventional non-ionic, anionic or cationic surface-active emulsifiers having an HLB (hydrophilic/lipophobic balance) value in the range of about 10 to 18, preferably about 13 to 16. The HLB value has been described in a publication of Atlas-Chemie, D-4300 Essen, published in the year 1968. The surface-active emulsifiers used may be compounds such as sodium propylnaphthalene sulphonate, polyoxyethylene sorbito-oleate-laurate, ethoxylated nonyl phenols, polyethylene glycol ethers of straight chained alcohols or polyethylene glycol esters of straight chained carboxylic acids. The emulsifier may be added not only to the aqueous phase (preferred) but also to the organic phase and is used in quantities of about 0.01 to 3.0% by weight, based on the aqueous phase.

The reaction of the organic polyisocyanate with water may be accelerated by adding the catalysts used in polyurethane chemistry in the known, catalytically active quantities, e.g. tertiary amines (N,N-dimethylbenzylamine, triethylamine, pyridine or bis-(dimethylaminoethyl)-ether) or organometallic compounds (tributyl tin acetate, di-n-butyl-tin diacetate, Sn(II)-dioctoate or dibutyl tin dilaurate). The catalyst is preferably added to the aqueous phase, but may alternatively be added only after the emulsion has formed. The quantity of catalyst is preferably chosen so that the reaction is completed after about 2 to 8 hours and the heat of reaction evolved does not heat the mixture to temperatures above about 35° C. so that no external cooling need be applied.

The reaction between the organic polyisocyanate and water can be seen from the evolution of $CO_2$. Disturbances due to foaming may be prevented by chemically binding the $CO_2$ by the addition of a base (e.g. aqueous sodium hydroxide solution) so that the reaction is carried out at a pH $\geq 7$ to 10 (preferably 8.5 to 9.5). Alternatively or in addition, a commercial antifoamant such as tributyl phosphate may be added.

After termination of the reaction, which may be seen from the cessation of evolution of $CO_2$, the suspension is suction filtered through a suitable filter and washed with water. It is then optionally again washed with a solvent which is inert towards isocyanates and may have a certain solubility in water, e.g. ethyl acetate or acetone, and it is finally dried in a drying cupboard, preferably under vacuum, at a low temperature (50° C.).

When tertiary amines are used as a catalyst, these may be completely transferred to the aqueous phase in the form of their salts by the addition of an equivalent quantity of acid so that they will no longer be present in the solid polyisocyanate containing urea groups after this product has been worked up. Other, known processes may also be employed for removing the catalyst. If desired, the reaction may be terminated before its completion by inactivating the catalyst.

When the process according to the invention is employed, the products are obtained in the form of virtually perfect spheres with particle diameters generally in the region of about 1 to 20 μm. The particle diameter is determined microscopically by comparison with a calibrated scale placed in the path of the beam.

The finely divided polyisocyanates containing urea groups prepared according to the invention are preferably used in formulations for polyurethane one-component systems based on stabilized solid, finely divided polyisocyanates which are covered in a shell of polyadduct and retarded in their reactivity, for example as described in DE-OS No. 3,230,757/EP-A No. 103,323; DE-OS No. 3,403,500/EP-A No. 150,790; DE-OS No. 3,418,430/EP-A No. 162,364; DE-OS No. 3,419,429/EP-A No. 165,437; DE-OS No. 3,112,054/EP-P No. 62,780; and DE-OS No. 3,343,124/EP-A No. 145,999. It is particularly advantageous that these finely divided polyisocyanates can be used in these one-component systems without first being ground down.

General description of the experimental method of carrying out the preparation of polyisocyanates containing urea groups The given quantity of water (preferably demineralized water) was homogeneously mixed in a glass beaker of suitable size with the given quantity of stabilizer solution, the given quantity of emulsifier, if used (preferably in the form of a dilute solution), the given quantity of catalyst, if used, and any other additives used, at room temperature or with slight cooling (about 15° C.).

The weighed quantity of polyisocyanate used as starting material was then added and either at the same time or thereafter the two-phase mixture was vigorously mixed with cooling by means of a Ultraturrax stirrer (Model T 45/N of IKA-Werk, Staufen im Breisgau with Generator 45 G 6) (speed setting at ⅓ to ⅔ of full power) until a stable emulsion had formed (generally about 3 minutes). This emulsion was transferred to a reaction flask with ground glass top and stirred with a conventional blade stirrer.

If the aqueous phase was initially added without catalyst, then the catalyst was added at this time. The evolution of $CO_2$ which set in as the reaction gradually began was measured with a gas meter. When evolution of $CO_2$ ceased, the reaction mixture was optionally neutralized (e.g. 1N HCl), and the suspension obtained was then suction filtered, washed with water and dried.

The yield was virtually quantitative since both the filter cake and the filtrate were virtually free from unreacted starting isocyanate.

The invention is further illustrated, but is not intended to be limited by the following examples in which all parts and percentages are by weight unless otherwise specified.

EXAMPLES

EXAMPLE 1

(a) Preparation of the polyisocyanate containing urea groups
Aqueous phase:
  700 g of water
  4.0 g of dispersion stabilizer solution prepared from
    15 g of glycine,
    56.2 g of tris(2-(hydroxyethoxy)-ethyl)amine,
    134.4 g of water and
    2.5 g of dimethyl-benzylamine as catalyst
Organic phase:
  150 g of 2,4-toluylene diisocyanate
Product:
  average particle size range: 8–14 μm
  isocyanate content: 23.62% by weight (b) Preparation of a polyurea polyurethane
100 parts of a polyoxypropylene glycol polyether containing terminal aromatic amino groups and having an NH number of 47.5 (prepared according to DOS No. 2,948,419 by the hydrolysis of a prepolymer obtained from 1 mol of polyoxypropylene glycol, molecular weight 2000, and 2 mol of 2,4-toluylene diisocyanate) were vigorously mixed with
19 parts of the polyisocyanate containing urea groups prepared in (a), using a powerful stirrer with a toothed rim stirrer disc and the mixture was degasified in a water jet vacuum.
A The "thickening temperature" of the mixture was then determined by the method described in DOS No. 3,230,757, page 49, and a sample plate measuring $20 \times 20 \times 0.3$ cm$^3$ was produced from the mixture on a metal casting mold (hardening of the liquid mixture in one hour at 150° C.).

B Another mixture was prepared in which 0.05 parts (to 100 parts of polyether) of a polyoxypropylene glycol containing terminal aliphatic amino groups were added to the polyoxypropylene polyether containing terminal amino groups before the polyisocyanate containing urea groups was added. The "thickening temperature" of this mixture was determined and a sample plate was again prepared. Table 1 shows the results obtained and the mechanical properties of the sample plates produced.

TABLE 1

|  | A | B |
| --- | --- | --- |
| Thickening Temperature | 68 | 82 |
| Mechanical properties: |  |  |
| Tensile strength | 13.89 | 12.53 |
| DIN 53504 (MPa) |  |  |
| 100% modulus | 13.89 | 11.96 |
| (DIN 53504) (MPa) |  |  |
| Elongation at break DIN 53504 (%) | 150 | 200 |
| Tear propagation resistance | 30.7 | 29.9 |
| DIN 53515 (kN/m) |  |  |
| Shore hardness A | 92 | 90 |
| DIN 53505 D | 40 | 40 |
| Elasticity | 44 | 46 |
| DIN 53512 (%) |  |  |
| Time for hardening | 1'20" | 1'50" |
| a sample 3 mm in thickness (min'/sec") |  |  |

The experiments show the excellent reactivity of the polyisocyanates prepared according to the invention (see thickening temperature in Experiments A and B) and the (desired) low sensitivity towards the aliphatic polyamines used for forming a reaction retarding polyurea outer shell.

EXAMPLE 2

Aqueous phase:
  3500 g of water
  20 g of stabilizer solution prepared from
    15 g of glycine
    29.8 g of triethanolamine and
    134.4 g of water
    12.5 g of dimethylbenzylamine as catalyst
Organic phase:
  750 g of 2,4-toluylene diisocyanate
Product:
  Particle size range: 6–14 μm
  NCO content: 24.30% by weight

EXAMPLE 3

Aqueous phase:
  3500 g of water
  20 g of stabilizer solution prepared from
    15 g of glycine,
    29.8 g of triethanolamine and
    134.4 g of water
    12.5 g of dimethylbenzylamine as catalyst
Organic phase:
  750 g of 2,4-toluylene diisocyanate
The catalyst was neutralized by the addition of an equivalent quantity of 1N-hydrochloric acid after termination of the reaction (cessation of $CO_2$ evolution).
Product:

average particle size range: 8–14 μm
NCO content: 23.63% by weight

EXAMPLE 4

Aqueous phase:
  3500 g of water
  20 g of stabilizer solution prepared from
    15 g of glycine
    29.8 g of triethanolamine and
    134.4 g of water
  10 g of 1,4-diazabicyclooctane as catalyst
Organic phase:
  750 g of 2,4-toluylene diisocyanate
Product:
  average particle size range: 5–14 μm
  NCO content: 24.23% by weight

EXAMPLE 5

Aqueous phase:
  3500 g of water
  5 g of stabilizer solution prepared from
    60.97 g of a 41% aqueous solution of the sodium salt of 2-aminoethanesulphonic acid and
    118.23 g of dimethylbenzylamine as catalyst
Organic phase:
  750 g of 2,4-toluylene diisocyanate
Product:
  average particle size range: 5–15 μm
  NCO content: 23.61% by weight

EXAMPLE 6

Aqueous phase:
  3500 g of water
  20 g of stabilizer solution prepared from
    29.05 g of 94.3% 4-aminobenzoic acid,
    29.8 g of triethanolamine
    and 120.4 g of water
  12.5 g of dimethylbenzylamine as catalyst
Organic phase:
  750 g of 2,4-toluylene diisocyanate
Product:
  average particle size range: 4–13 μm
  NCO content: 23.49% by weight

EXAMPLE 7

Aqueous phase:
  3500 g of water
  20 g of stabilizer solution prepared from
    26.2 g of 6-aminohexanoic acid,
    29.8 g of triethanolamine and
    123.2 g of water
  12.5 g of dimethylbenzylamine as catalyst
Organic phase:
  750 g of 2,4-toluylene diisocyanate
Product:
  average particle size range: 5–15 μm
  NCO content: 24.18% by weight

EXAMPLE 8

Aqueous phase:
  3500 g of water
  20 g of stabilizer solution prepared from
    17.8 g of 3-aminopropanoic acid,
    29.8 g of triethanolamine and
    131.6 g of water
  12.5 g of dimethylbenzylamine as catalyst
Organic phase:
  750 g of 2,4-toluylene diisocyanate
Product:
  particle size range: 7–14 μm
  NCO content: 23.48% by weight

EXAMPLE 9

Aqueous phase:
  700 g of water
  4 g of stabilizer solution prepared from
    34.6 g of 4-aminobenzene sulphonic acid,
    29.8 g of triethanolamine and
    114.8 g of water
  2.5 g of dimethylbenzylamine as catalyst
Organic phase:
  150 g of 2,4-toluylene diisocyanate
Product:
  average particle size range: 7–14 μm
  NCO content: 24.10% by weight

EXAMPLE 10

Aqueous phase:
  3500 g of water
  20 g of stabilizer solution prepared from
    15 g of glycine,
    22.4 g of 50% aqueous KOH solution and
    141.8 g of water
  12.5 g of dimethylbenzylamine as catalyst
Organic phase:
  750 g of 2,4-toluylene diisocyanate
Product:
  particle size range: 7–14 μm
  NCO content: 22.99% by weight

EXAMPLE 11

Aqueous phase:
  3500 g of water
  20 g of stabilizer solution being a
    40% solution of Na-hydrogen sulphite in water
  12.5 g of dimethylbenzylamine as catalyst
Organic phase:
  750 g of 2,4-toluylene diisocyanate
Product:
  particle size range: 6–15 μm
  NCO content: 24.04% by weight

EXAMPLE 12

Aqueous phase:
  700 g of water
  2.5 g of stabilizer solution prepared from
    18.4 g of mercaptoacetic acid,
    29.8 g of triethanolamine and
    131.0 g of water
Organic phase:
  150 g of 2,4-toluylene diisocyanate
  1 g of dimethylbenzylamine as catalyst was added 1.5 hours after emulsification
Product:
  particle size range: 7–12 μm
  NCO content: 22.70% by weight

EXAMPLE 13

Aqueous phase:
  357 g of water
  2 g of stabilizer solution prepared from
    125 g of 80% lactic acid,
    20.2 g of triethylamine and
    136.5 g of water
Organic phase:
  75 g of 2,4-toluylene diisocyanate 1.25 g of dimethylbenzylamine as catalyst was added 30 minutes after emulsification.
Product:
 particle size range: 2–12 μm
 NCO content: 21.00% by weight

EXAMPLE 14

Aqueous phase:
 3500 g of water
 20 g of stabilizer solution prepared from
  20.4 g of N,N-dimethyl-1,3-diaminopropane,
  12.0 g of acetic acid and
  146.8 g of water
 12.5 g of dimethylbenzylamine as catalyst
Organic phase:
 750 g of 2,4-toluylene diisocyanate
Product:
 particle size range: 3–12 μm
 NCO content: 23.06% by weight

EXAMPLE 15

Aqueous phase:
 3500 g of water
 20 g of stabilizer solution prepared from
  20.4 g of N,N-dimethyl-1,3-diaminopropane,
  17.0 g of cyanoacetic acid and
  141.8 g of water
 12.5 g of dimethylbenzylamine as catalyst
Organic phase:
 750 g of 2,4-toluylene diisocyanate
Product:
 particle size range: 5–15 μm
 NCO content: 23.72% by weight

EXAMPLE 16

Aqueous phase:
 3500 g of water
 20 g of stabilizer solution prepared from
  20.4 g of N,N-dimethyl-1,3-diaminopropane,
  22.5 g of 80% lactic acid and
  140.8 g of water
 12.5 g of dimethylbenzylamine as catalyst
Organic phase:
 750 g of 2,4-toluylene diisocyanate
Product:
 particle size range: 5–13 μm
 NCO content: 23.00% by weight

EXAMPLE 17

Aqueous phase:
 375 g of water
 1.0 g of 1-amino-8-hydroxy-3,6-dioxa-octane
 12.5 g of dimethylbenzylamine as catalyst
Organic phase:
 75 g of 2,4-toluylene diisocyanate
Product:
 particle size range: 10–18 μm
 NCO content: 23.30% by weight

EXAMPLE 18

Aqueous phase:
 3500 g of water
 14 g of di(hydroxyethyl)amine as stabilizer
 12,5 g of dimethylbenzylamine as catalyst
Organic phase:
 750 g of 2,4-toluylendiisocyanate
Product:
 particle-size range: 8–15 μm
 NCO-content: 23,30% by weight.

EXAMPLE 19

Aqueous phase:
 3500 g of water
 3,4 g of Hydroxyethylamine as stabilizer
 12,5 g of dimethylbenzylamine as catalyst
Organic phase:
 750 g of 2,4-toluylendiisocyanate
Product:
 particle size range: 9–18 μm
 NCO-content: 24,03% by weight.

EXAMPLE 20

Aqueous phase:
 3500 g of water
 5 g of N,N-Dimethyl-1,3-diaminopropane(1-Amino-3-(dimethylamino)propane)
Organic phase:
 750 g of 2,4-Toluylendiisocyanate
Product:
 particle size range 2–15 μm
 NCO-content: 23,36% by weight.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for the preparation of finely divided, solid polyisocyanates containing urea groups which comprises reacting water with an organic polyisocyanate which is free from urea groups in an aqueous emulsion and optionally in the presence of emulsifiers, catalysts, and/or bases, which further comprises conducting the reaction in the presence of an emulsion- and dispersion-stabilizing compound corresponding to the formula (I)

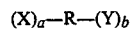

wherein
X denotes an $NH_2$ group, a $NHR^1$ group in which $R^1$ represents a $C_1$- to $C_{10}$-alkyl group which optionally contains a tert. amino groups, an OH-group or an SH-group,
R denotes an aromatic group with 6 to 20 carbon atoms, a heteroaromatic group with 5 to 20 carbon atoms and at least one oxygen and/or nitrogen atom in the ring system, an aliphatic group with 2 to 20 carbon atoms or a cycloaliphatic group with 4 to 20 carbon atoms, said groups being optionally substituted with halogen atoms,
Y denotes COOH, or $COO^-M^+$ in which M stands for an alkali metal, an alkaline earth metal, $NH_4$ or the group $NH-(R^2)_3$ in which $R^2$ represents hydroxyalkyl, alkoxyalkyl or alkyl with 1 to 10 carbon atoms; or Y denotes $SO_3H$ or $SO_3^-M^+$ in which M is as defined above as indicated; or Y denotes $-N(R^2)_2$ or $-N^\oplus H(R^2)_2 Z^\ominus$ in which Z is a carboxylate group or a sulphonate group and $R^2$ is as defined above; or Y denotes a group corresponding to the formula (II)

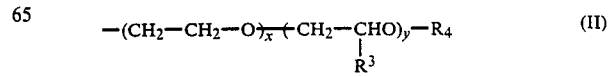

wherein
R$^3$ denotes a C$_1$–C$_6$-alkyl group,
R$^4$ denotes hydrogen or a C$_1$–C$_6$-alkyl group and
x and y, which may be identical or different, each represents an integer with a value or 0 to 50 (sum of x+y is at least 1) and
a and b, which may be identical or different each represent an integer with a value of 1 to 3, provided that
  (i) when Y denotes OH or SH, then R is neither an aromatic nor a heteroaromatic group, and
  (ii) when Y is a group of the general formula (II), then X may only denote NH$_2$ or NHR$^2$ and R must stand for a chemical bond,
or the reaction is carried out in the presence of an alkali metal hydrogen sulphite.

2. The process of claim 1 wherein the stabilizing compound used is a compound corresponding to the general formula (I) in which
X denotes NH$_2$ and Y denotes COOH, COO$^\ominus$M$^\oplus$, SO$_3$H or SO$_3^\ominus$M$^\oplus$, or
X denotes NH$_2$ or OH and Y denotes —N$^\oplus$H(R$^2$)$_2$Z$^\ominus$ or
X denotes OH or SH and Y denotes COO$^\ominus$M$^\oplus$.

3. The process of claim 1 wherein said stabilizing compound comprises
  (a) a carboxylic acid selected from the group consisting of 2-, 3- and 4-aminobenzoic acid, 4-chloranthranilic acid, 6-chloranthranilic acid, 3-amino-4-methylbenzoic acid, 3-aminocinnamic acid, 5-aminoisophthalic acid, 3-aminosalicylic acid, 4-aminosalicylic acid, 5-aminosalicylic acid, aminoacetic acid, N-methylaminoacetic acid, 3-aminopropionic acid, 4-aminobutanoic acid, 6-aminohexanoic acid, L(+)-2,6-diaminohexanoic acid, 11-aminoundecanoic acid, L(+)-aminobutane diacid, L(+)-aminopentane diacid and DL-methiamine,
  (b) an alkali metal and alkaline earth metal salt of said carboxylic acid,
  (c) a salt of said carboxylic acid with a tertiary amine,
  (d) a sulfonic acid selected from the group consisting of 2-, 3-, and 4-aminobenzene sulphonic acid, 3-amino-6-chlorobenzene sulphonic acid, p-phenylenediamine-2-sulphonic acid, 4-aminotoluene-2-sulphonic acid, 5-aminotoluene-2-sulphonic acid, 2-aminotoluene-4-sulphonic acid, 3-aminobenzyl sulphonic acid, 4-aminobenzyl sulphonic acid, naphthionic acid, 2-aminoethane sulphonic acid, 2-methylaminoethane sulphonic acid, and 2-butylaminoethane sulphonic acid,
  (e) an alkali metal and alkaline earth metal salt of said sulphonic acid,
  (f) a salt of said sulphonic acid with a tertiary amine,
  (g) an ammonium salt of an amine containing at least one OH group, primary amino group and/or secondary amino group and at least one tertiary amino group and a quantity of carboxylic or sulphonic acid such that at least one NCO-reactive group per molecule remains,
  (h) a salt of a hydroxycarboxylic acid or a mercaptocarboxylic acid, and a tertiary amine, or
  (i) sodium hydrogen sulphite.

4. The process of claim 3 wherein said tertiary amine comprises a member selected from the group consisting of trimethylamine, triethylamine, dimethylbenzylamine, tris-hydroxyethylamine, tris-[(2-hydroxyethoxy)ethyl]-amine and triethylenediamine.

5. The process of claim 1 wherein said stabilizing compound comprises a salt of 2-(N,N-dimethylamino)-ethanol, 2-(N,N-dimethylamino)isoproponal, or 2-(N,N-dimethylaminoethoxy)-ethanol and acetic acid, propionic acid, benzoic acid, or lactic acid.

6. The process of claim 1 wherein said stabilizing compound comprises a salt of a hydroxycarboxylic acid or mercaptocarboxylic acid which comprises a member selected from the group consisting of lactic acid, glycolic acid, citric acid, dimethylolpropionic acid, tartaric acid and mercaptoacetic acid and a tertiary amine which comprises a member selected from the group consisting of trimethylamine, triethylamine, dimethylbenzylamine, tris-hydroxyethylamine, tris-[(2-hydroxyethoxy)ethyl]-amine and triethylenediamine.

7. The process of claim 1 wherein said stabilizing compound comprises a salt of N,N-dimethyl-1,3-propylene diamine and one equivalent of acetic acid, propionic acid, lactic acid, dimethylolpropionic acid, methane sulfonic acid, butane sulfonic acid or 2-hydroxyethane sulfonic acid.

8. The process of claim 1 wherein said stabilizing compound is used in a quantity of about 0.01 to 5% by weight, based on the polyisocyanate which is free from urea groups.

9. The process of claim 2 wherein said stabilizing compound is used in a quantity of about 0.01 to 5% by weight, based on the polyisocyanate which is free from urea groups.

10. The process of claim 3 wherein said stabilizing compound is used in a quantity of about 0.01 to 5% by weight, based on the polyisocyanate which is free from urea groups.

11. The process of claim 4 wherein said stabilizing compound is used in a quantity of about 0.01 to 5% by weight, based on the polyisocyanate which is free from urea groups.

12. A process for the preparation of finely divided, solid polyisocyanates containing urea groups which comprises reacting water with an organic polyisocyanate which is free from urea groups in an aqueous emulsion and optionally in the presence of emulsifiers, catalysts, and/or bases, which further comprises conducting the reaction in the presence of an emulsion- and dispersion-stabilizing compound corresponding to the formula (I)

(X)$_a$—R—(Y)$_b$  (I)

wherein
X denotes an NH$_2$ group, a NHR$^1$ group in which R$^1$ represents a C$_1$- to C$_{10}$-alkyl group, an OH group or an SH group,
R denotes an aromatic group with 6 to 20 carbon atoms, a heteroaromatic group with 5 to 20 carbon atoms and at least one oxygen and/or nitrogen atom in the ring system, an aliphatic group with 2 to 20 carbon atoms or a cycloaliphatic group with 4 to 20 carbon atoms, said groups being optionally substituted with halogen atoms,
Y denotes COOH, or COO$^-$M$^+$ in which M stands for an alkali metal, an alkaline earth metal, NH$_4$ or the group NH—(R$^2$)$_3$ in which R$^2$ represents hydroxyalkyl, alkoxyalkyl or alkyl with 1 to 10 carbon atoms; or Y denotes SO$_3$H or SO$_3^-$M$^+$ or in which M is as defined above as indicated; or Y denotes —NH(R$^2$)$_2$Z$^\ominus$ in which Z is a carboxylate group or a sulphonate group and R$^2$ is as defined above; or Y denotes a group corresponding to the formula (II)

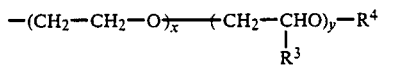

wherein
$R^3$ denotes a $C_1$-$C_6$-alkyl group,
$R^4$ denotes hydrogen or a $C_1$-$C_6$-alkyl group and
x and y, which may be identical or different, each represents an integer with a value of 0 to 50 and
a and b, which may be identical or different each represent an integer with a value of 1 to 3, provided that
(i) when Y denotes OH or SH, then R is neither an aromatic nor a heteroaromatic group, and
(ii) when Y is a group of the general formula (II), then X may only denote $NH_2$ or $NHR^2$ and R must stand for a chemical bond, or the reaction is carried out in the presence of an alkali metal hydrogen sulphite.

13. The process of claim 12 wherein the stabilizing compound used is a compound corresponding to the general formula (I) in which X denotes $NH_2$ and Y denotes COOH, $COO^\ominus M^\oplus$, $SO_3H$ or $SO_3^\ominus M^\oplus$, or X denotes $NH_2$ or OH and Y denotes $-NH(R^2)_2$-$Z^\ominus$ or X denotes OH or SH and Y denotes $COO^\ominus M^\ominus$.

14. The process of claim 12 wherein said stabilizing compound comprises
(a) a carboxylic acid selected from the group consisting of 2-, 3- and 4-aminobenzoic acid, 4-chloranthranilic acid, 6-chloranthranilic acid, 3-amino-4-methylbenzoic acid, 3-aminocinnamic acid, 5-aminoisophthalic acid, 3-aminosalicyclic acid, 4-aminosalicylic acid, 5-aminosalicylic acid, aminoacetic acid, N-methylaminoacetic acid, 3-aminopropionic acid, 4-aminobutanoic acid, 6-aminohexanoic acid, L(+)-2,6-diaminohexanoic acid, 11-aminoundecanoic acid, L(+)-aminobutane diacid, L(+)-aminopentane diacid and DL-methiamine,
(b) an alkali metal and alkaline earth metal salt of said carboxylic acid,
(c) a salt of said carboxylic acid with a tertiary amine,
(d) a sulfonic acid selected from the group consisting of 2-, 3-, and 4-aminobenzene sulphonic acid, 3-amino-6-chlorobenzene sulphonic acid, p-phenylenediamine-2-sulphonic acid, 4-aminotoluene-2-sulphonic acid, 5-aminotoluene-2-sulphonic acid, 2-aminotoluene-4-sulphonic acid, 3-aminobenzyl sulphonic acid, 4-aminobenzyl sulphonic acid, naphthionic acid, 2-aminoethane sulphonic acid, 2-methylaminoethane sulphonic acid, and 2-butylaminoethane sulphonic acid,
(e) an alkali metal and alkaline earth metal salt of said sulphonic acid,
(f) a salt of said sulphonic acid with a tertiary amine,
(g) an ammonium salt of an amine containing at least one OH group, primary amino group and/or secondary amino group and at least one tertiary amino group and a quantity of carboxylic or sulphonic acid such that at least one primary and/or secondary amino group per molecule is not converted into the salt form,
(h) a salt of hydroxycarboxylic acid or a mercaptocarboxylic acid, and a tertiary amine, or
(i) sodium hydrogen sulphite.

15. The process of claim 14 wherein said tertiary amine comprises a member selected from the group consisting of trimethylamine, triethylamine, dimethylbenzylamine, tris-hydroxyethylamine, tris-[(2-hydroxyethoxy)ethyl]-amine and triethylenediamine.

16. The process of claim 12 wherein said stabilizing compound comprises a salt of 2-(N,N-dimethylamino)-ethanol, 2-(N,N-dimethylamino)-isopropanol, or 2-(N,N-dimethylaminoethoxy)-ethanol and acetic acid, propionic acid, benzoic acid, or lactic acid.

17. The process of claim 12 wherein said stabilizing compound comprises a salt of a hydroxy-carboxylic acid or mercaptocarboxylic acid which comprises a member selected from the group consisting of lactic acid, glycollic acid, citric acid, dimethylol-propionic acid, tartaric acid and mercaptoacetic acid and a tertiary amine which comprises a member selected from the group consisting of trimethylamine, triethylamine, dimethylbenzylamine, tris-hydroxyethylamine, tris-[(2-hydroxyethoxy)-ethyl]-amine and triethylenediamine.

18. The process of claim 12 wherein said stabilizing compound comprises a salt of N,N-dimethyl-1,3-propylene diamine and one equivalent of acetic acid, propionic acid, lactic acid, dimethylolpropionic acid, methane sulfonic acid, butane sulfonic acid or 2-hydroxyethane sulfonic acid.

19. The process of claim 12 wherein said stabilizing compound is used in a quantity of about 0.01 to 5% by weight, based on the polyisocyanate which is free from urea groups.

20. The process of claim 13 wherein said stabilizing compound is used in a quantity of about 0.01 to 5% by weight, based on the polyisocyanate which is free from urea groups.

21. The process of claim 14 wherein said stabilizing compound is used in a quantity of about 0.01 to 5% by weight, based on the polyisocyanate which is free from urea groups.

22. The process of claim 15 wherein said stabilizing compound is used in a quantity of about 0.01 to 5% by weight, based on the polyisocyanate which is free from urea groups.

* * * * *